(12) United States Patent
Rioux et al.

(10) Patent No.: US 7,481,798 B2
(45) Date of Patent: Jan. 27, 2009

(54) DEVICES AND METHODS FOR DELIVERING THERAPEUTIC OR DIAGNOSTIC AGENTS

(75) Inventors: Robert Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 115 days.

(21) Appl. No.: 10/846,476

(22) Filed: May 13, 2004

(65) Prior Publication Data

US 2004/0215130 A1 Oct. 28, 2004

Related U.S. Application Data

(63) Continuation-in-part of application No. 10/392,545, filed on Mar. 20, 2003.

(51) Int. Cl.
*A61M 5/00* (2006.01)

(52) U.S. Cl. .................. 604/256; 604/264

(58) Field of Classification Search ................
604/167.01–167.04, 164.06, 244–246, 256,
604/264, 268, 272, 278, 523, 537, 21, 27,
604/30, 32–35, 39, 43–44, 40, 506, 508,
604/265, 890.1
See application file for complete search history.

(56) References Cited

U.S. PATENT DOCUMENTS

| | | | | |
|---|---|---|---|---|
| 3,736,939 A | * | 6/1973 | Taylor | 604/265 |
| 4,127,133 A | | 11/1978 | Martinez | |
| 4,848,344 A | * | 7/1989 | Sos et al. | 606/194 |
| 4,935,006 A | * | 6/1990 | Hasson | 604/43 |
| 5,066,278 A | * | 11/1991 | Hirschberg et al. | 604/256 |
| 5,167,625 A | * | 12/1992 | Jacobsen et al. | 604/891.1 |
| 5,358,792 A | * | 10/1994 | Mehta et al. | 428/516 |

(Continued)

FOREIGN PATENT DOCUMENTS

WO    WO 00/67647    11/2000

(Continued)

OTHER PUBLICATIONS

PCT International Search Report for PCT/US04/003147, Applicant: Scimed Life Systems, Inc., Forms PCT/ISA/210 and 220, dated Jun. 21, 2004 (8 pages).

(Continued)

*Primary Examiner*—Nicholas D Lucchesi
*Assistant Examiner*—Theodore J Stigell
(74) *Attorney, Agent, or Firm*—Vista IP Law Group LLP

(57) ABSTRACT

An agent delivery device includes an inner tubular body having a proximal end, a sharpened distal end, a delivery lumen extending therebetween, and one or more outlet ports on the distal end communicating with the delivery lumen. The device also includes one or more seals sealing the one or more outlet ports, the one or more seals capable of being melted to allow a fluid to be delivered from the delivery lumen through the one or more outlet ports. The agent delivery device may further include a monopolar or bipolar electrode and/or a radio-opaque marker carried at the distal end of the device. The inner tubular body can be made from a conductive material to thereby allow the inner tubular body to function as an electrode.

29 Claims, 6 Drawing Sheets

U.S. PATENT DOCUMENTS

| | | | |
|---|---|---|---|
| 5,403,311 | A | 4/1995 | Abele et al. |
| 5,500,012 | A | 3/1996 | Brucker et al. |
| 5,522,815 | A | 6/1996 | Durgin, Jr. et al. |
| 5,536,242 | A * | 7/1996 | Willard et al. ............ 604/30 |
| 5,609,629 | A * | 3/1997 | Fearnot et al. ............ 623/1.42 |
| 5,718,702 | A | 2/1998 | Edwards |
| 5,749,914 | A | 5/1998 | Janssen |
| 5,843,050 | A * | 12/1998 | Jones et al. ............ 604/525 |
| 6,010,476 | A | 1/2000 | Saadat |
| 6,106,524 | A * | 8/2000 | Eggers et al. ............ 606/50 |
| 6,319,230 | B1 | 11/2001 | Palasis et al. |
| 6,461,296 | B1 | 10/2002 | Desai |
| 6,582,423 | B1 | 6/2003 | Thapliyal et al. |
| 6,695,822 | B2 * | 2/2004 | Adams et al. ............ 604/268 |
| 2002/0055712 | A1 | 5/2002 | Neracher |
| 2002/0055729 | A1 | 5/2002 | Goll |
| 2003/0028172 | A1 | 2/2003 | Epstein et al. |
| 2004/0087828 | A1 | 5/2004 | Green et al. |

FOREIGN PATENT DOCUMENTS

| | | | |
|---|---|---|---|
| WO | WO 01/41656 | * | 6/2001 |
| WO | WO 01/41656 A1 | | 6/2001 |

OTHER PUBLICATIONS

PCT Written Opinion of the International Search Authority for PCT/US04/003147, Application: Scimed Life Systems, Inc., Form PCT/ISA/237, dated Jun. 21, 2004 (5 pages).

PCT International Search Report for PCT/US2005/015893, Applicant: Boston Scientific Scimed, Inc., Form PCT/ISA/210 and 220, dated Jan. 3, 2006 (8 pages).

PCT Written Opinion of the International Search Authority for PCT/US2005/015893, Applicant: Boston Scientific Scimed, Inc., Form PCT/ISA/237, dated Jan. 3, 2006 (5 pages).

Examiner's Answer dated Aug. 21, 2007 to Appeal Brief for related U.S. Appl. No. 10/395,545, filed Mar. 20, 2003, Inventor: Robert Rioux (13 pages).

Advisory Action dated Jul. 24, 2007 for related U.S. Appl. No. 10/926,853, filed Aug. 25, 2004, Inventor: Robert Rioux (3 pages).

PCT International Search Report for PCT/US2004/003147, Applicant: Scimed Life Systems, Inc., Forms PCT/ISA/210 and 220, dated Jun. 21, 2004 (8 pages).

PCT Written Opinion of the International Search Authority for PCT/US2004/003147, Applicant: Scimed Life Systems. Inc., Form PCT/ISA/237, dated Jun. 21, 2004, (5 pages).

PCT International Preliminary Report on Patentability for PCT/US2004/003147, Applicant: Boston Scientific Limited, Form PCT/IB/326, dated Oct. 6, 2005 (7 pages).

Office Action dated May 14, 2007 for related U.S. Appl. No. 10/926,853, filed Aug. 25, 2004, Inventor: Robert F. Rioux (7 pages).

PCT International Search Report for PCT/US2005/029699, Applicant: Boston Scientific Scimed, Inc., Form PCT/ISA/210 and 220, dated Jul. 5, 2006 (9 pages).

PCT Written Opinion of the International Search Authority for PCT/US2005/029699, Applicant: Boston Scientific Scimed, Inc., Form PCT/ISA/237, dated Jul. 5, 2006 (7pages).

Final Office Action dated Nov. 30, 2004 from related U.S. Appl. No. 10/392,545, filed Mar. 20, 2003, Inventor: Robert Rioux et al. (6 pages).

Advisory Action dated Feb. 10, 2005 from related U.S. Appl. No. 10/395,545 filed Mar. 20, 2003, Inventor: Robert Fioux et al. (2 pages).

Notification of Non-Compliant Appeal Brief dated Jul. 12, 2005 from related U.S. Appl. No. 10/392,545, filed Mar. 20, 2003, Inventor: Robert Rioux et al. (1 page).

Advisory Action dated Jul. 24, 2007 from related U.S. Appl. No. 10/926,853, filed Aug. 25, 2004, Inventor: Robert Rioux (3 pages).

Office Action dated May 14, 2007 for related U.S. Appl. No. 10/926,853, filed Aug. 25, 2004, Inventor: Robert F. Rioux (7 pages).

Non-Final Office Action dated Nov. 22, 2006, for related U.S. Appl. No. 10/926,853 filed Aug. 25, 2004, Inventor: Robert Rioux et al. (7 pages).

* cited by examiner

DEVICES AND METHODS FOR DELIVERING THERAPEUTIC OR DIAGNOSTIC AGENTS

This application is a continuation-in-part of U.S. patent application Ser. No. 10/392,545, filed Mar. 20, 2003, the disclosure of which is expressly incorporated by reference herein.

FIELD OF THE INVENTION

The field of the invention relates to medical devices, and, more particularly, to apparatus and methods for delivering therapeutic or diagnostic agents to a site within tissue.

BACKGROUND

Medical needles have been used to deliver therapeutic or diagnostic agents to a target site within tissue for treatment or diagnostic purposes. Needles typically have a tubular body for delivering an agent, and a sharp distal tip for puncturing skin and/or other bodily tissues, thereby creating a needle tract through intervening tissues between the skin and the target site.

Before the tip of the needle reaches the target site, i.e., while the needle is advanced through intervening tissue, there is a risk that the agent may leak out of the distal tip of the needle and into the intervening tissue. Since the agent may be sclerotic, necrotic, and/or toxic to living tissue, if the agent leaks or spreads, it may damage the intervening tissue.

After an agent is delivered to the target site, the needle is typically withdrawn, thereby leaving the created tract through the tissues that eventually closes up through normal healing. However, before the tract is healed, the agent(s) delivered to the target site may leak into the tract, possibly spreading the agent(s) to surrounding tissue. As discussed previously, since the agent may be toxic to living tissue, allowing the agent to spread may damage the surrounding tissue. For example, when treating a prostate with Ethanol, significant amounts of the infused Ethanol may leak through the needle tract, possibly damaging unintended tissue.

Furthermore, when a needle is used to deliver an agent to a tumor, tumor cells may be released into surrounding tissue simply by perforating the tumor with the needle. For example, tumor cells may migrate into the needle tract and into surrounding healthy tissue through the needle tract. This phenomenon is known as "tract seeding."

Thus, apparatus and methods for delivering an agent to a site that minimize the agent leaking and/or tumor cells migrating to surrounding tissue would be useful.

SUMMARY OF THE INVENTION

The present invention is directed to apparatus and methods for delivering therapeutic or diagnostic agents to a target site within tissue.

In accordance with one aspect of the present invention, an apparatus is provided that may include an inner tubular body having a proximal end, a sharpened distal end, a delivery lumen extending therebetween, and one or more outlet ports on the distal end communicating with the delivery lumen. The apparatus may also include one or more seals sealing the one or more outlet ports. The seal may be melted to allow fluid to be delivered from the delivery lumen through the outlet port(s). In one embodiment, the seal may have a melting temperature of at least about fifty degrees Celsius (50° C.), and, preferably, at least about seventy degrees Celsius (70° C). In another embodiment, the seal may have a melting temperature that is between about 70° C. and about 100° C. In another embodiment, the seal may have a melting temperature that is close to a temperature at which tissue desiccation may occur.

Optionally, the apparatus may also include an outer tubular body having a proximal end, a distal end, an aspiration lumen extending therebetween, and one or more aspiration ports on the distal end communicating with the aspiration lumen. The inner tubular body may be slidably received in the outer tubular body such that the distal end of the inner tubular body may be advanced beyond the distal end of the outer tubular member. Optionally, one or more stops may be provided on one or both of the inner and outer tubular bodies for limiting advancement and/or retraction of the inner tubular body relative to the outer tubular body.

Optionally, the apparatus may include a source of agent coupled to the proximal end of the inner tubular body such that the source of agent may communicate with the delivery lumen, and/or a source of vacuum coupled to the proximal end of the outer tubular body such that the source of vacuum may communicate with the aspiration lumen. For example, the agent may be a cooling fluid, conductive fluid, therapeutic agent, or diagnostic agent.

In addition, the apparatus may include one or more of the following: an electrode or a radio-opaque marker. For example, one or more electrodes may be provided on at least one of the distal end of the outer tubular body and the distal end of the inner tubular body. A source of electrical energy, e.g., a radio frequency ("RF") generator, may be coupled to the electrode(s). In addition or alternatively, a radio-opaque marker may be provided on at least one of the distal end of the outer tubular body and the distal end of the inner tubular body, and preferably on both the inner and outer tubular bodies. In another embodiment, instead of carrying an electrode, the inner tubular member of the apparatus may be made from an electrically conductive material to allow the inner tubular member itself to function as an electrode.

In accordance with yet another aspect of the present invention, a method is provided for delivering an agent to a target site within tissue. A needle may be advanced through intervening tissue to a target site, thereby creating a tract through the intervening tissue, the needle including one or more outlet ports sealed by one or more seals. The seal may be melted to allow an agent to be delivered via the needle to the target site.

In accordance with another embodiment, a method for delivering an agent to a target site within tissue may include advancing an apparatus including inner and outer elongate members through intervening tissue until distal ends of the inner and outer members are located adjacent a target site, thereby creating a tract through the intervening tissue. The inner elongate member may include a lumen and one or more outlet ports sealed by one or more seals. The seals may be melted, e.g., by delivering electrical energy to heat and the seal (s), to allow an agent to be delivered via the lumen of the inner elongate member through the outlet port(s) to the target site. Before, during, and/or after delivering the agent, material that enters the tract from the target site may be aspirated into the outer member.

Other aspects and features of the invention will be evident from reading the following detailed description of the preferred embodiments, which are intended to illustrate, but not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not intended to limit its scope, the invention will be described and explained with additional specificity and detail through the use of the accompanying drawings.

DETAILED DESCRIPTION OF THE PREFERRED EMBODIMENTS

Figure 1:
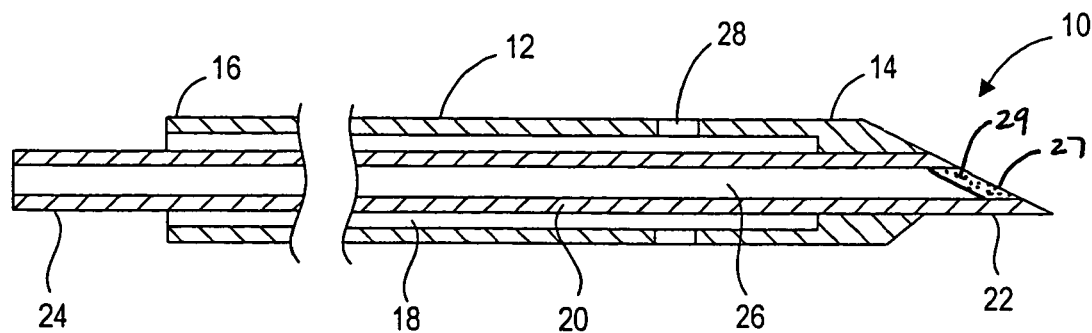
FIG. 1 is a cross-sectional side view of a first embodiment of an apparatus for delivering an agent into tissue, in accordance with the present invention.

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate describing specific embodiments of the invention. They are not intended as an exhaustive description of the invention or as a limitation on the scope of the invention. In addition, an illustrated embodiment need not have all aspects or advantages of the invention shown. An aspect or an advantage described in conjunction with a particular embodiment of the present invention is not necessarily limited to that embodiment and may be practiced in any other embodiments of the present invention even if not so illustrated.

FIG. 1 shows an agent delivery device 10 constructed in accordance with an embodiment of the present invention. The agent delivery device 10 includes an outer tubular body 12 having a proximal end 16, a distal end 14, a lumen 18 extending between the proximal and distal ends 16, 14, and one or more suction or aspiration ports 28 located at or near the distal end 14 of the outer tubular body 12. The agent delivery device 10 also includes an inner tubular body 20, such as a needle, positioned coaxially within the lumen 18 of the outer tubular body 12. The inner tubular body 20 has a distal end 22, a proximal end 24, a lumen 26 extending between the distal and the proximal ends 22 and 24, and an outlet port 27 at the distal end 22 that is in fluid communication with the lumen 26. The agent delivery device 10 also includes a seal 29 sealing the outlet port 27. The aspiration port 28 and the seal 29 are discussed in further detail below.

The outer tubular body 12 may be made from a variety of materials, such as plastics, polymers, metals, alloys, graphite, and/or composites of such materials. In the illustrated embodiment, the distal end 14 of the outer tubular body 12 has a cross section that is thicker than the rest of the outer tubular body 12, thereby maintaining the inner tubular body 20 substantially coaxially within the lumen 18 of the outer tubular body 12. The proximal end 16 of the outer tubular body 12 is configured to be coupled to a source of vacuum (not shown) that may generate a vacuum within the lumen 18, i.e., within the annular space between the outer tubular body 12 and the inner tubular body 20, that is substantially isolated from the lumen 26 of the inner tubular body 20. Any source of vacuum, e.g., a syringe, a vacuum line, or a pump, may be used, as is generally well known in the art. The aspiration port 28 at or near the distal end 14 of the outer tubular body 12 communicates with the lumen 18 of the outer tubular body 12. When a vacuum is created within the lumen 18 of the outer tubular body 12, fluid or objects outside the outer tubular body 12 may be aspirated into the lumen 18 through the aspiration port 28.

The source of vacuum may be coupled to the proximal end 16 of the outer tubular body 12 using any known manner, e.g., depending on the cross-sectional shape of the outer tubular body 12 and the configuration of the source of vacuum. For example, the proximal end 16 of the outer tubular body 12 may include a connector, e.g., a male or female luer lock connector (not shown), that may substantially seal the lumen 18 at the proximal end of the outer tubular body 12 when connected to the source of vacuum. A section of tubing and the like that communicates with the source of vacuum may include a complementary connector that may engage the connector on the proximal end 16 of the outer tubular member 12. Alternatively, the proximal end 16 of the outer tubular member 12 may be closed, and a nipple or other side port may be provided on the outer tubular member 12 that communicates with the lumen 18. The manner in which the source of vacuum is coupled to the proximal end 16 is not critical to the present invention.

In the illustrated embodiment, the distal end 22 of the inner tubular body 20 may have a tissue piercing tip and/or a low profile that may facilitate penetrating the inner tubular body 20 through skin or other bodily tissues. The proximal end 24 of the inner tubular body 20 is configured to be coupled to a source of fluid, such as a therapeutic and/or diagnostic agent, which may include genetic material and implantable cells for gene/cell therapy. For example, the proximal end 24 of the inner tubular body 20 may include a connector (not shown) that may be coupled to a syringe, bottle, bag, or other container including the agent therein. Any of the materials discussed previously with reference to the outer tubular body 12 may also be suitable for construction of the inner tubular body 20. It should be understood by those skilled in the art that the flexibility or stiffness of the agent delivery device 10 may be varied by using different materials for the outer and/or inner tubular bodies 12, 20.

Figure 2:
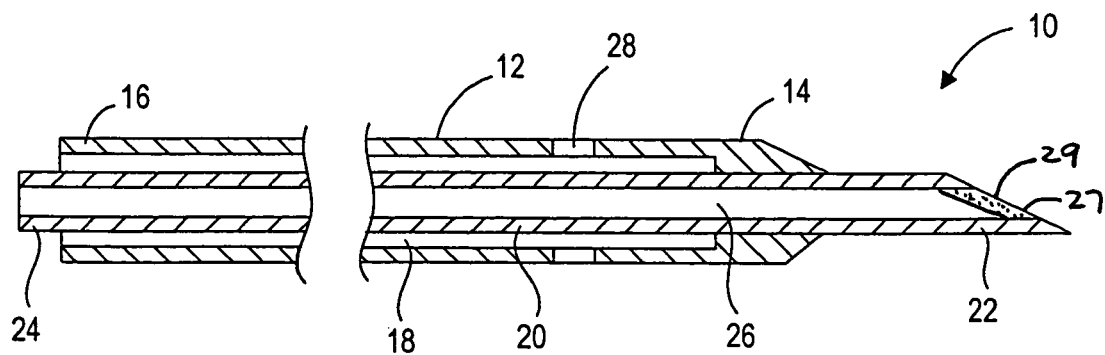
FIG. 2 is a cross-sectional side view of the apparatus of FIG. 1, showing an inner tubular body extending distally relative to an outer tubular body.

The inner tubular body 20 is preferably slidable axially relative to the outer tubular body 12. FIG. 2 shows the inner tubular body 20 advanced distally relative to the outer tubular body 12. The agent delivery device 10 may include one or more cooperating stops (not shown), e.g., secured to the proximal end 24 of the inner tubular body 20 and/or the outer tubular body 12 to prevent the inner tubular body 20 from being advanced beyond a predetermined distance relative to the outer tubular body 12.

In the illustrated embodiment, the seal 29 substantially covers the outlet port 27 such that material within the lumen 26 of the inner tubular body 20 cannot escape from the outlet port 27. During use, heat may be delivered to melt the seal 29, thereby allowing material within the lumen 26 of the inner tubular body 20 to be delivered through the outlet port 27. Towards this end, the seal 29 may be made from a material that may be melted when subjected to heat that is at least about fifty degrees Celsius (50° C.), and, preferably, at least about seventy degrees Celsius (70° C.). In another embodiment, the seal 29 can be made from a material having a melting point that is between about 70° C. and about 100° C. Suitable materials may include wax (such as medical grade paraffin), gels that have reduced viscosity when heated, polymers, and other suitable materials. Depending on the particular application, a desired melting point of the seal 29 may be achieved by varying a composition of the materials from which the seal 29 is made. The seal 29 may be a plug that may be inserted into the outlet port 27 during manufacturing, and/or before or after a fluid or other material is introduced into the lumen 26 of the inner tubular body 20. The seal 29 may be secured within the outlet port 27 by friction or a suitable adhesive. Alternatively, the distal end 22 of the inner tubular body 20 may be dipped into a heated liquid or other solution to introduce the solution into the outlet port 27. The solution may be cooled and/or cured to solidify the solution, thereby forming the seal 29 in the outlet port 27. Other methods for creating the seal 29 and/or securing the seal 29 to the inner tubular body 20 may also be used.

Figure 3:
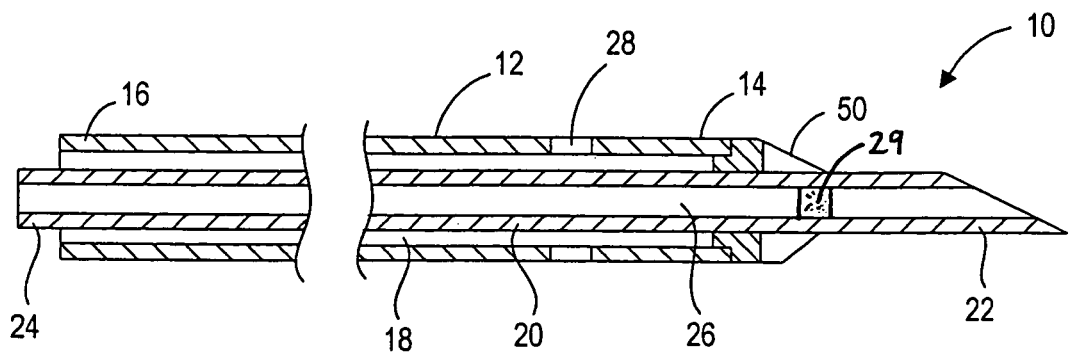
FIG. 3 is a cross-sectional side view of a variation of the apparatus of FIG. 1, showing the apparatus including an electrode carried at its distal end.

As shown in FIG. 3, optionally, the agent delivery device 10 may include one or more electrodes 50 carried at the distal end 14 of the outer tubular body 12. In this case, the seal 29 may be positioned such that when the inner tubular body 20 extends distally from the distal end 14 of the outer tubular body 12 by a certain prescribed distance, the seal 29 may be adjacent to the electrode(s) 50. This configuration may provide a shorter path for the heat generated by the electrode 50 to reach the seal 29. Alternatively, if the inner tubular body 20 is made from a material that is conductive to heat, the seal 29 may be placed further away from the electrode(s) 50. In this case, heat generated by the electrode 50(s) may be conducted by the inner tubular body 20, and transmitted to the seal 29. In another embodiment, the electrode(s) 50 may be carried at the distal end 22 of the inner tubular body 20. Besides being used to melt the seal 29, the electrode(s) 50 may also be used to ablate tissue in a monopolar or bipolar manner, as is known in the art. In yet another embodiment, either or both of the outer tubular body 12 and the inner tubular body 20 may be made from an electrically conductive material, in which case, either or both of the outer and inner tubular bodies 12, 20 may be used to generate heat (e.g., in a bi-polar or monopolar arrangement) to melt the seal 29.

Figure 4:
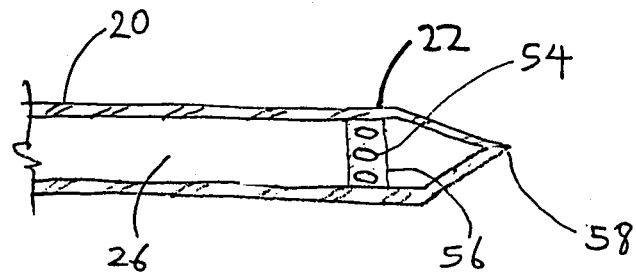
FIG. 4 is a cross-sectional detail of a variation of the apparatus of FIGS. 1 and 2, showing the inner tubular body having side ports.

In the previously described embodiments, the outlet port 27 may be located at the distal tip of the inner tubular body 20. However, in alternative embodiments, the inner tubular body 20 may include one or more outlet ports 27 that are at other locations of the inner tubular body 20. FIG. 4 shows a variation of the inner tubular body 20 having one or more outlet ports 54 located in the side wall(s) of the inner tubular body 20. The outlet port(s) 54 may be located at or near the distal end 22 of the inner tubular body 20 for delivering an agent therethrough. The outlet port(s) 54 may have different shapes other than the circular shape shown in the illustrated embodiment. For example, the delivery port(s) 54 may have an elliptical shape, rectangular shape, or other customized shape. In the illustrated embodiment, the outlet port(s) 54 may be sealed by a single seal 56. Alternatively, each of the outlet ports 54 may be sealed by a respective seal 56. The seal 56 may be secured to the tubular body 20 by any of the methods described previously. Optionally, the tubular body 20 may include a sharp distal tip 58 for piercing tissue.

Figure 5:
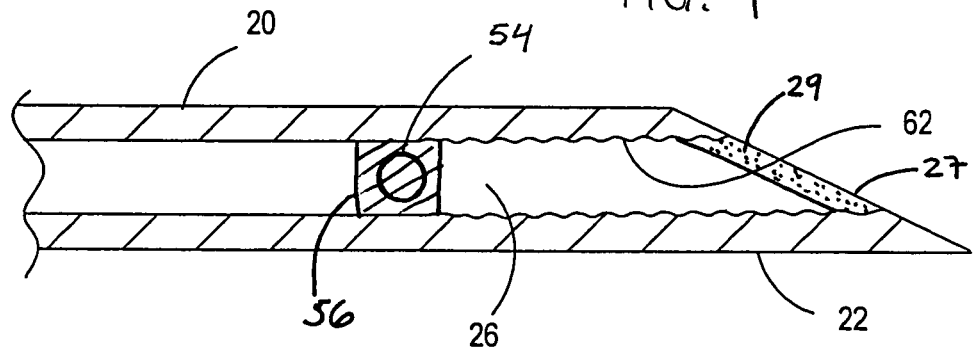
FIG. 5 is a cross-sectional detail of a variation of the apparatus of FIGS. 1 and 2, showing the inner tubular body having a textured interior surface and a side port.

FIG. 5 shows a variation of an inner tubular body 20 that includes both an outlet port 27 at the distal tip of the inner tubular body 20, and one or more side outlet ports 54 located along a side wall of the inner tubular body 20. As discussed previously, the outlet port 27 may be sealed by the seal 29, and the side outlet port(s) 54 may be sealed by the seal 56. Alternatively, a single seal may be used to seal both the outlet port 27 and the side outlet port(s) 54. In addition or alternatively, an interior surface 62 of a distal portion of the lumen 26 of the inner tubular body 20 may be textured (e.g., roughened), to retain tissue that may enter the distal portion of the lumen 26 therein, e.g., while the agent is being delivered through the outlet port(s) 54.

Figure 6:
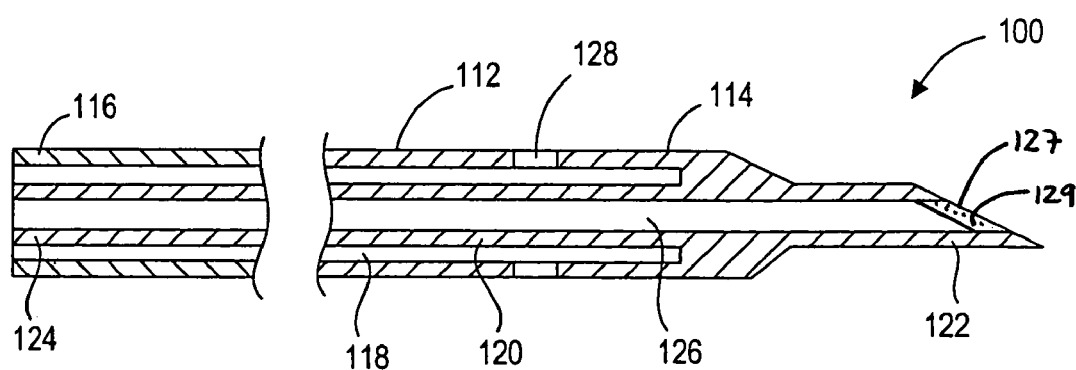
FIG. 6 is a cross-sectional side view of another embodiment of an apparatus, in accordance with the present invention, including an inner tubular body fixed relative to an outer tubular body.

In the previously described embodiments, the inner tubular body 20 may be slidable relative to the outer tubular body 12. However, the scope of the invention should not be so limited. For example, FIG. 6 shows an agent delivery device 100 including an outer tubular body 112 having a proximal end 116, a distal end 114, a lumen 118 extending therebetween, and one or more suction ports 128 located at or near the distal end 114 of the outer tubular body 112. The agent delivery device 100 may also include an inner tubular body 120 positioned coaxially within the lumen 118 of the outer tubular body 112. The inner tubular body 120 has a distal end 122, a proximal end 124, a lumen 126 extending between the distal and the proximal ends 122 and 124, and an outlet port 127 at the distal end 122 that is in fluid communication with the lumen 126. The agent delivery device 100 may also include a seal 129 covering the outlet port 127.

The only difference between the embodiment shown in FIG. 6 and that shown in FIG. 1 is that the inner tubular body 120 is fixed relative to the outer tubular body 112. This may be accomplished using glue, solder, or other suitable adhesive between the outer and inner tubular bodies 112, 120, depending on the materials from which they are made. The outer and inner tubular bodies 112, 120 may also be constructed or formed as a single unit during manufacturing.

As shown in FIG. 6, the distal end 114 of the outer tubular body 112 may be secured to the inner tubular body 120 at a location proximal to the distal end 122 of the inner tubular body 112. Alternatively, as shown in FIG. 7, the distal end 114 of the outer tubular body 112 may be secured to the distal end 122 of the inner tubular body 112 so that the agent delivery device 100 has a substantially smooth and continuous exterior profile along a length of the agent delivery device 100.

Figure 7:
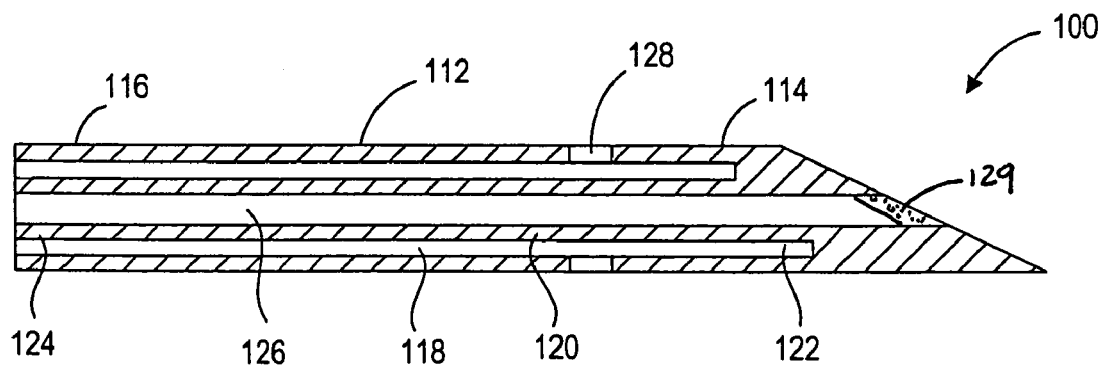
FIG. 7 is a cross-sectional side view of a variation of the apparatus of FIG. 6.

In either of the embodiments shown in FIGS. 6 and 7, the agent delivery device 100 may include one or more electrodes 50, as discussed previously with reference to FIG. 3. Furthermore, the agent delivery device 100 may also include one or more side outlet ports and/or a textured interior surface at the distal end 122 of the inner tubular body 120, as discussed previously with reference to FIGS. 4 and 5.

In any of the embodiments discussed previously, the agent delivery device 10/100 may include one or more radio-opaque markers carried at the distal end of the agent delivery device 10/100, such as at the distal end 22/122 of the inner tubular body 20/120, and/or at the distal end 14/114 of the outer tubular body 12/112. The radio-opaque marker(s) may assist monitoring the agent delivery device 10/100 as it is manipulated or positioned during a procedure, as is known in the art.

Figure 8A:
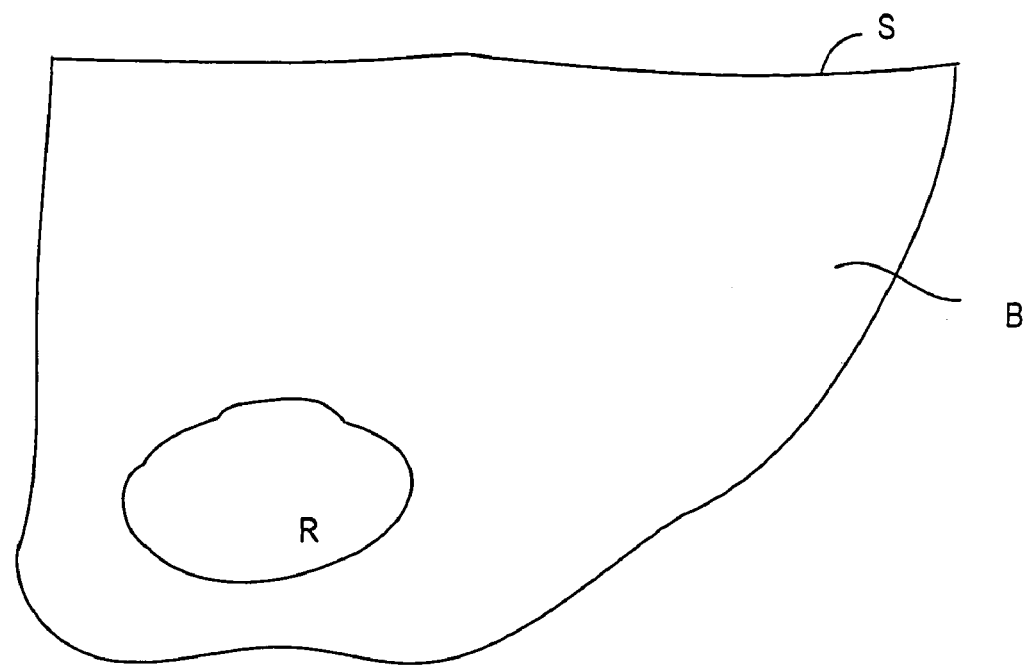
FIGS. 8A-8D are cross-sectional views showing a method for using an apparatus to deliver an agent into tissue.

Referring now to FIGS. 8A-8D, the agent delivery device 10 (or other devices described above) may be used to treat or diagnose a target region R within tissue located beneath the skin S and intervening tissue B of a patient. FIG. 8A shows the region R before the procedure. The proximal end (not shown) of the inner tubular body 20 may be coupled to a source of agent, and/or the proximal end (not shown) of the outer tubular body 12 may be coupled to a source of vacuum.

Figure 8B:
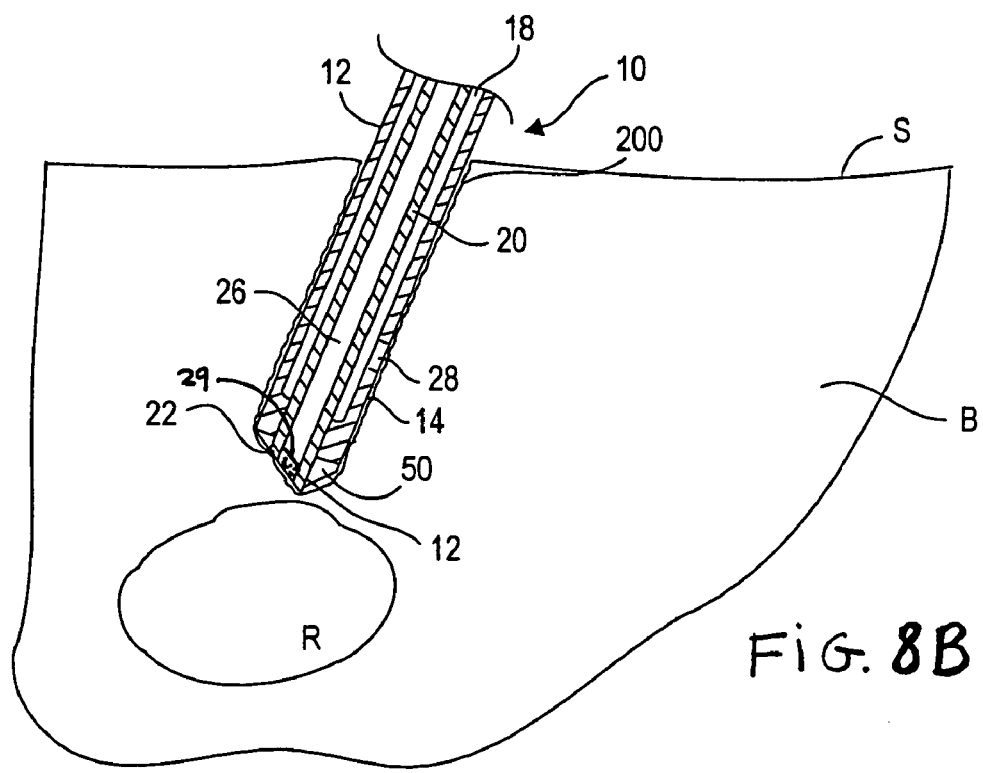

As shown in FIG. 8B, the distal end 22 of the inner tubular member 20 may be retracted at least partially into the distal end 14 of the outer tubular member 12. The device 10 may then be advanced through the skin S and intervening tissue B until the distal ends 22, 14 are located adjacent to the region R. Preferably, the sharp distal end 22 of the inner tubular body 20 facilitates penetrating the skin S and intervening tissue B, thereby creating a tract or pathway 200 leading to the region R. The seal 29 may prevent material, such as a toxic drug and/or other diagnostic and/or therapeutic agent, from prematurely or accidentally escaping from the lumen 26 of the inner tubular body 20 as the device 10 is advanced through the skin S and intervening tissue B. The seal 29 may also function as an anti-coring device by preventing a sample or an object from entering the inner tubular body 20 during use.

Figure 8C:
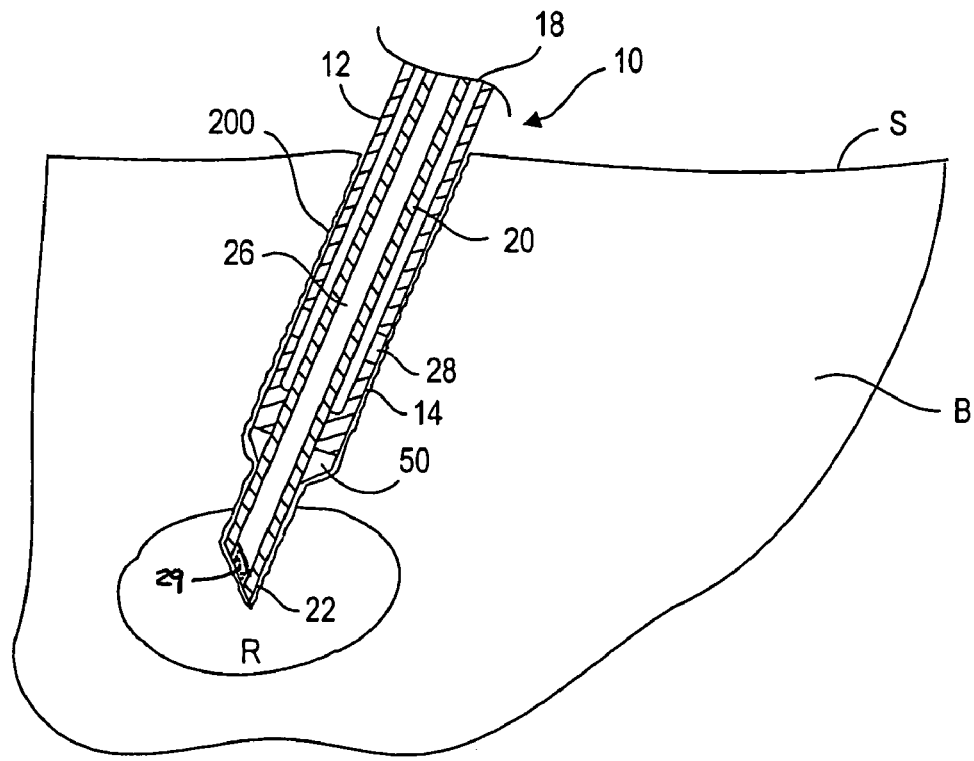

As shown in FIG. 8C, once the distal end 14 of the outer tubular body 12 is positioned adjacent to the region R, the distal end 22 of the inner tubular body 20 may be advanced distally into the region R. Alternatively, the distal end 14 of the outer tubular body 12 may be positioned within the region R, and the inner tubular body 20 may be advanced such that the distal end 22 extends further into the region R. If the agent delivery device 10 includes one or more radio-opaque markers, the marker(s) may be used to assist positioning the distal ends 14, 22 of the agent delivery device 10. In a further alternative, if a device 100, such as that shown in FIGS. 6 or 7, is used that includes an inner tubular body 120 fixed to an outer tubular body 112, the device 100 may be advanced distally until the distal end 122 reaches the region R. Optionally, as shown in FIG. 5, if the inner tubular body 20 includes a textured interior surface 62, tissue may enter at least partially into the lumen 26 as the inner tubular body 20 is advanced into the region R. This may allow a portion of tissue from the region R to be retrieved, e.g., for a biopsy or other analysis.

Returning to FIG. 8C, once the distal end 22 of the inner tubular body 20 is positioned within the region R, one or more electrodes 50 may be energized to deliver electrical energy to generate heat to melt the seal 29. In the illustrated embodiment, heat may be conducted by the inner tubular body 20 and/or by surrounding tissue, and transmitted to the seal 29. After the seal 29 is melted, the agent within the lumen 26 may be delivered into the region R via the lumen 26 and distal end 22 of the inner tubular body 20. If the inner tubular body 20 includes one or more side ports 54, such as that shown in FIGS. 4 and 5, heat generated by the electrode(s) 50 may also melt the seal(s) 56 sealing the side port(s) 54, thereby allowing the agent to exit from the side ports 54.

As the agent is being delivered into the region R, some of the agent may seep or otherwise leak into the tract 200. If the source of vacuum is not already creating a vacuum within the lumen 18 of the outer tubular body 12, the source may be activated to create a vacuum and aspirate the agent entering the tract 200 into the lumen 18 through the aspiration port(s) 28. Preferably, the source of vacuum is activated before the agent delivery device 10 is inserted into the patient so that any fluid that enters the tract 200 is aspirated. Alternatively, the source of vacuum may be activated at any time during the procedure, e.g., at periodic time intervals.

Figure 8D:
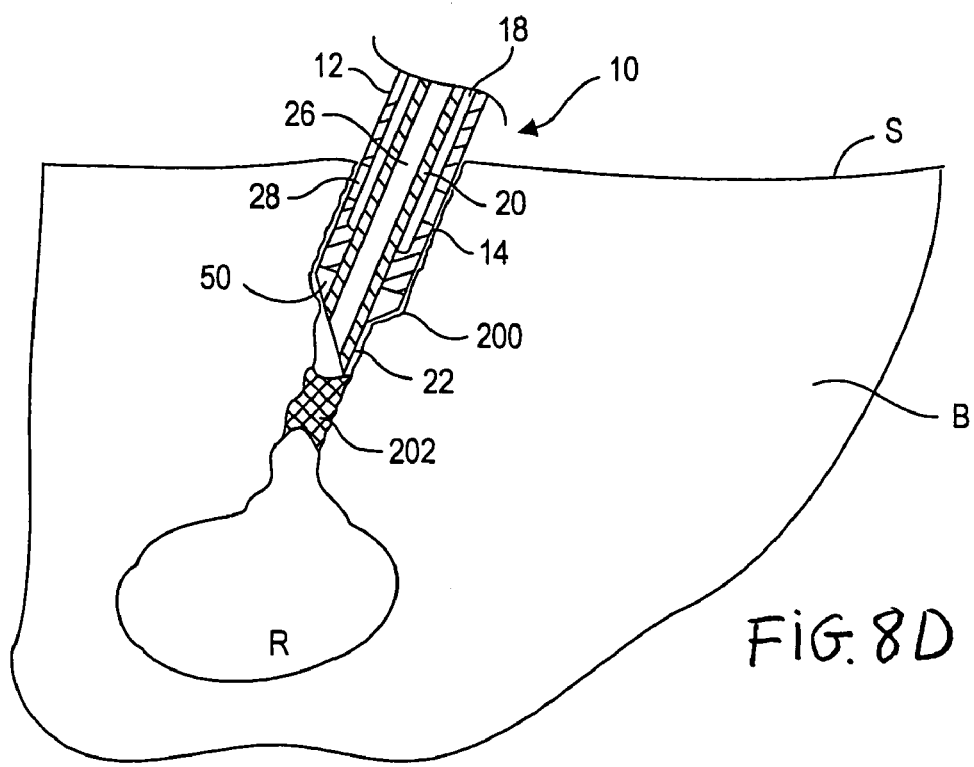

Turning to FIG. 8D, the inner tubular body 20 may be retracted proximally relative to the outer tubular body 12, e.g., to withdraw the distal end 22 of the inner member 20 into the outer tubular member 12. The agent delivery device 10 may then be withdrawn proximally from the tract 200 and the patient. If tissue is captured within the lumen 26 of the inner tubular body 20 (e.g., by the interior surface 62), it may be separated from the remaining tissue within the region R and removed from the patient as the device 10 is removed.

If the agent delivery device 10 includes one or more electrodes, such as the electrode 50 shown in FIG. 3, energy may be delivered via the electrode(s) 50 to treat the tissue surrounding the tract 200. For example, the electrode(s) 50 may deliver radio frequency (RF) electrical energy to coagulate, ablate, or otherwise treat the surrounding tissue to substantially seal or occlude the tract 200. In one embodiment, only the tissue at region 202 adjacent the region R may be treated, which may be sufficient to prevent the agent leaking from the region R and/or tumor cells migrating into the tract 200. Alternatively, energy may be delivered to additional tissue along the tract 200, e.g., in short bursts such that spaced-apart regions are treated. In another alternative, energy may be delivered substantially continuously as the device 10 is withdrawn to substantially seal the tract 200 along all or part of its length. Thus, the tract 200 may be substantially sealed, thereby preventing or reducing the risk of tract seeding from a tumor and/or contaminating tissue surrounding a target region to which the agent is delivered.

Figure 9:
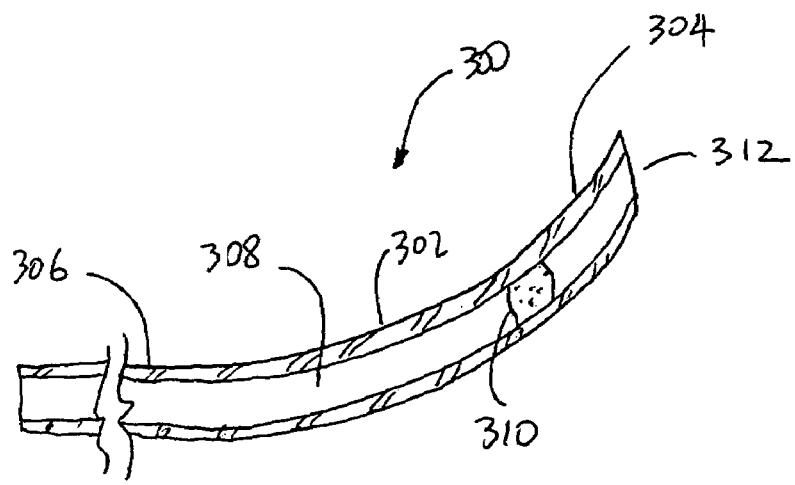
FIG. 9 is a cross sectional view of another embodiment of an agent delivery device.

It should be noted that although the seal 29 (or 129) has been described with reference to the agent delivery device 10 (or 100), in alternative embodiments, the same or similar seal may also be incorporated into other types of medical devices having fluid delivery capability. FIG. 9 shows another agent delivery device 300 that has tissue ablation capability. The agent delivery device 300 may include a tubular body 302 having a distal end 304, a proximal end 306, and a lumen 308 extending between the distal and proximal ends 304, 306. The tubular body 302 may have a curvilinear profile. Alternatively, the tubular body 302 may also have a rectilinear profile or other shapes. The agent delivery device 300 may not include an outer tubular body, and therefore, may not include a fluid aspiration ability. However, in another embodiment, the agent delivery device 300 may also include an outer tubular body, as discussed previously. The agent delivery device 300 may also include a seal 310 disposed within the lumen 308 of the tubular body 302 to prevent material from exiting through a distal opening 312. The construction and operation of the seal 310 may be similar to the embodiments discussed previously, e.g., to the seal 29 of FIG. 1. In the illustrated embodiment, the tubular body 302 may be made from a material that is electrically conductive, thereby allowing the tubular body 302 itself to function as an ablative electrode. Materials suitable for constructing the tubular body 302 may include stainless steel, Nitinol, and/or other metals. The tubular electrode body 302 may operate in a bipolar, or monopolar arrangement.

Figure 10A:
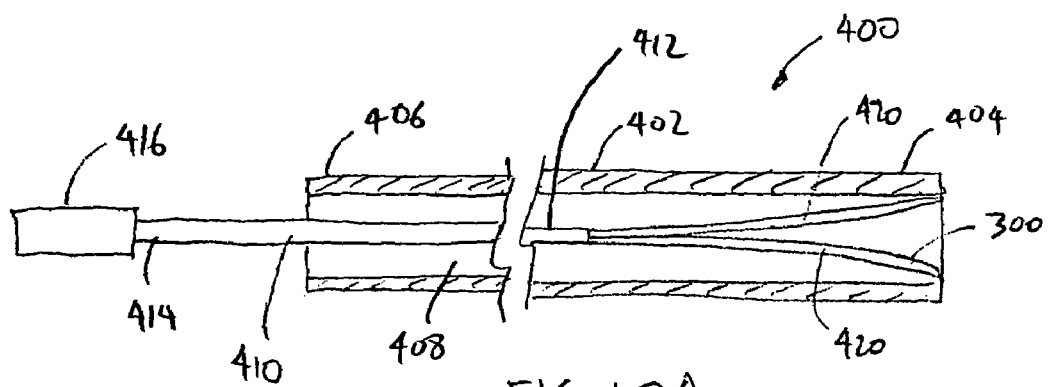
FIG. 10A is a cross sectional view of an ablation probe that includes the agent delivery device of FIG. 9, showing the agent delivery device confined within a lumen of the ablation probe.
Figure 10B:
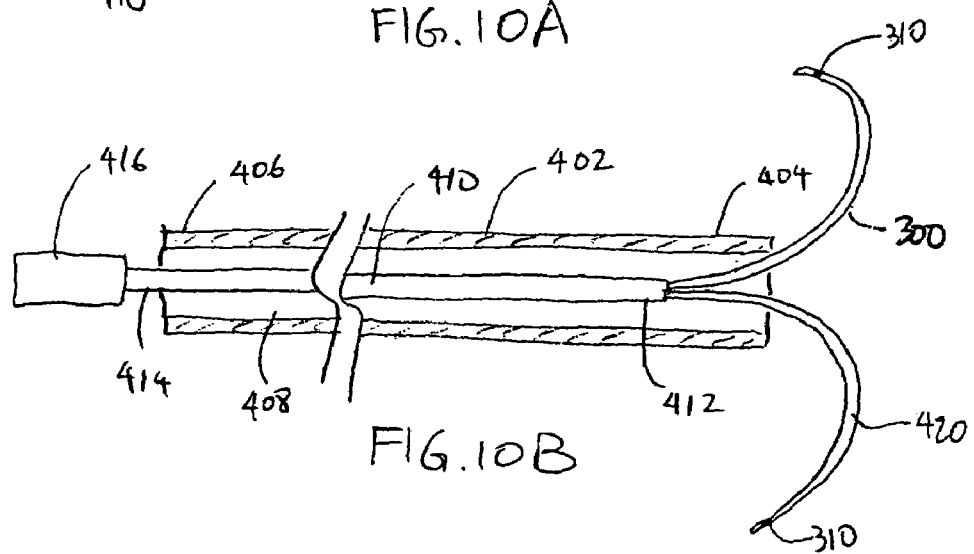
FIG. 10B is a cross sectional view of the ablation probe of FIG. 10A, showing at least a portion of the agent delivery device outside the lumen of the ablation probe.

As shown in FIGS. 10A and 10B, in one embodiment, the agent delivery device 300 may be an ablation electrode that is a part of an ablation probe 400. The ablation probe 400 may include a shaft 402 having a distal end 404, a proximal end 406, and a lumen 408 extending between the distal and proximal ends 404, 406. The ablation probe 400 may also include an elongate member 410 having distal and proximal ends 412, 414, a handle 416 on the proximal end 414, and a plurality of elongated electrodes 420. Each of the electrodes 420 may include the agent delivery device 300 of FIG. 9. As shown in FIG. 10A, each of the electrodes 420 may have a low profile when confined within the lumen 408 of the shaft 402. During use, the handle 416 may be used to advance the electrodes 420 relative to the shaft 410. When the electrodes 420 are at least partially outside the lumen 408 of the shaft 420, they may assume a relaxed and/or expanded configuration, such as that shown in FIG. 10B. Similar ablation probes have been described in U.S. Pat. No. 5,855,576, the entire disclosure of which is expressly incorporated by reference herein.

During use, the distal end 404 of the shaft 402 may be inserted into a patient, and advanced until it is adjacent target tissue, such as a tumor. The handle 416 may then be advanced relative to the shaft 402 to deploy the electrodes 420 (i.e., the tubular body 302) outside the distal end 404 of the shaft 402. The distal end 304 of the tubular body 302 may have a sharp distal tip allowing the distal end 304 to pierce into the target tissue, thereby creating a tract within the target tissue. Electrical energy may then be delivered to the tubular body 302 to ablate the target tissue. During ablation, the temperature of tissue adjacent the tubular body 302 may reach up to about ninety degrees Celsius (90° C.), at which point, the target tissue may begin to dessicate. This desiccation may create gas bubbles and/or increase impedance at the tissue-electrode interface, the occurrence of which may prevent or reduce heat from being delivered by the electrodes 420 to the target tissue.

As the target tissue is being ablated, the temperature at the tubular body 302 may also rise, causing the seal 310 to heat up. In the illustrated embodiment, the seal 310 has a designed melting temperature that approximates the temperature above which tissue desiccation may occur. For example, the seal 310 may have a melting temperature that is higher than about fifty degrees Celsius (50° C.), and preferably, higher than about seventy degrees Celsius (70° C.). When the temperature of the seal 310 reaches its designed melting temperature, the seal 310 may melt, allowing a material, such as cooling fluid, to be delivered from within the lumen 308 of the tubular member 302 to a space within the created tract, and more particularly, to the interface between the tubular member 302 and the target tissue.

Using cooling fluid in association with delivering electrical energy is known to force the electrode-tissue interface to lower temperature values. As a result, the hottest tissue temperature region is shifted deeper into the tissue, which, in turn, shifts the boundary of the tissue rendered nonviable by ablation further away from the ablating tubular body 302. An electrode that is actively cooled may be used to transmit more ablation energy into the tissue, compared to the-same electrode that is not actively cooled. The cooling fluid may be saline and/or other biocompatible agent. Electrically conductive fluid (i.e., fluid that contains ions) may also be used. Using conductive fluid may further enhance transmission of radio frequency ("RF") energy between the tubular body 302 and another electrode, such as an adjacent electrode (as in the case for bipolar arrangement), or an indifferent electrode placed on a patient's skin (as in the case for monopolar arrangement). When a desired lesion has been created by the ablating tubular body 302, the tubular body 302 is then removed from the target tissue and the patient.

Although several embodiments of the agent deliver device have been described, it should be noted that the scope of the invention should not be so limited, and that variations and modifications of the previously described embodiments are intended to be within the scope of the invention. For example, instead of carrying an electrode, the agent delivery device may carry other heat generating devices or mechanisms for delivering heat to the seal, e.g., electrically resistive elements, lasers or other fiber optic elements, and the like. Also, in alternative embodiments, the heat being used to melt the seal does not have to be generated by an electrode that is a part of the agent delivery device. Instead, the heat may be generated by an electrode or other heat generating mechanism that is located on another device, e.g., introduced in close proximity and/or in cooperation with the agent delivery device. In this case, the agent delivery device may not include an electrode.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. An apparatus for delivering a therapeutic or diagnostic agent to a target site within tissue, comprising:
 a tubular body comprising a proximal end, a sharpened distal end, a delivery lumen extending therebetween, and one or more outlet ports on the distal end communicating with the delivery lumen; and
 one or more seals sealing the one or more outlet ports to prevent leakage of a fluid from the delivery lumen out of the distal end of the tubular body, the one or more seals incapable of passing a fluid when intact, the one or more seals capable of being melted to allow a fluid to be delivered from the delivery lumen through the one or more outlet ports, the one or more seals having a melting point greater than body temperature, wherein the one or more seals have a melting point equal to one hundred degrees Celsius (100°C.) or less.

2. The apparatus of claim 1, wherein the one or more seals have a melting point between fifty degrees Celsius (50°C.) and one hundred degrees Celsius (100°C.).

3. The apparatus of claim 1, further comprising a source of agent coupled to the proximal end of the tubular body such that the source of agent communicates with the delivery lumen.

4. The apparatus of claim 1, further comprising one or more electrodes on the distal end of the tubular body.

5. The apparatus of claim 4, wherein the one or more electrodes are configured for melting the one or more seals when electrical energy is delivered to the one or more electrodes.

6. The apparatus of claim 1, wherein the one ormore outlet ports comprise one or more outlets ports comprise one or more openings in a side wall of the tubular body.

7. The apparatus of claim 1, wherein the distal end of the tubular body comprises an axial opening communicating with the delivery lumen, an interior surface of the tubular body being textured for retaining tissue that enters the axial opening.

8. The apparatus of claim 1, further comprising an outer tubular body having a proximal end, a distal end, an aspiration lumen extending therebetween, and one or more aspiration ports on the distal end communicating with the aspiration lumen, the tubular body slidably received in the outer tubular body such that the distal end of the tubular body is advanceable beyond the distal end of the outer tubular member.

9. The apparatus of claim 8, further comprising a source of vacuum coupled to the proximal end of the outer tubular body such that the source of vacuum communicates with the aspiration lumen.

10. The apparatus of claim 8, further comprising one or more electrodes on the distal end of the outer tubular body.

11. The apparatus of claim 10, further comprising a source of electrical energy coupled to the one or more electrodes.

12. The apparatus of claim 1, wherein the one or more seals are affixed to the tubular body.

13. The apparatus of claim 12, wherein the one or more seals are bonded to the tubular body.

14. The apparatus of claim 1, wherein the one or more seals are disposed within the delivery lumen.

15. An apparatus for delivering a therapeutic or diagnostic agent to a target site within tissue, comprising:
- an elongate body comprising a proximal end, a distal end terminating in a tissue piercing distal tip, a delivery lumen extending from the proximal end to one or more outlet ports adjacent the distal tip, one or more seals sealing the one or more outlet ports to prevent leakage of a fluid from the delivery lumen out through the distal end of the elongate body, the one or more seals capable of being melted to allow the fluid to be delivered from the delivery lumen through the one or more outlet ports, and an aspiration lumen extending from the proximal end to one or more inlet ports on the distal end proximal to the one or more outlet ports, wherein the one or more seals have a melting point egual to one hundred degrees Celsius (100°C) or less;
- a source of therapeutic or diagnostic agent communicating with the delivery lumen for delivering the agent through the delivery lumen to the one or more outlet ports; and
- a source of vacuum communicating with the aspiration lumen for aspirating material adjacent the one or more inlet ports into the aspiration lumen.

16. The apparatus of claim 15, wherein the one or more seals have a melting point between body temperature and one hundred degrees Celsius (100°C).

17. The apparatus of claim 15, wherein the one or more seals have a melting point between fifty degrees Celsius (50°C) and one hundred degrees Celsius (100°C).

18. The apparatus of claim 15, further comprising one or more electrodes associated with the distal end.

19. The apparatus of claim 18, wherein the one or more electrodes are at the distal end.

20. The apparatus of claim 18, wherein the one or more electrodes are positioned at a distance from the seal such that heat generated by the one or more electrodes can cause the seal to melt.

21. The apparatus of claim 18, further comprising a source of electrical energy coupled to the one or more electrodes.

22. The apparatus of claim 15, wherein the one or more outlet ports comprise one or more openings in a side wall at the distal end of the elongate body.

23. The apparatus of claim 15, wherein the distal tip comprises an axial opening communicating with the delivery lumen, an interior surface of the distal tip being textured for engaging tissue that enters the axial opening.

24. The apparatus of claim 15, wherein the distal tip is movable axially relative to the one or more inlet ports.

25. The apparatus of claim 15, wherein the aspiration lumen comprises an annular lumen.

26. The apparatus of claim 15, wherein the one or more seals are incapable of passing a fluid when intact.

27. The apparatus of claim 15, wherein the one or more seals are affixed to the elongate body.

28. The apparatus of claim 27, wherein the one or more seals are bonded to the elongate body.

29. The apparatus of claim 15, wherein the one or more seals are disposed within the delivery lumen.

* * * * *

UNITED STATES PATENT AND TRADEMARK OFFICE
CERTIFICATE OF CORRECTION

PATENT NO. : 7,481,798 B2  Page 1 of 1
APPLICATION NO. : 10/846476
DATED : January 27, 2009
INVENTOR(S) : Robert Rioux et al.

It is certified that error appears in the above-identified patent and that said Letters Patent is hereby corrected as shown below:

Col. 10, Claim 6, Line 49, replace "ormore" with --or more--
Col. 11, Claim 15, Line 25 replace "egual" with --equal--

Signed and Sealed this

Fourteenth Day of July, 2009

JOHN DOLL
*Acting Director of the United States Patent and Trademark Office*